United States Patent
Constantz et al.

(10) Patent No.: US 8,728,026 B2
(45) Date of Patent: May 20, 2014

(54) DEVICES AND METHODS FOR TREATING AORTIC VALVE STENOSIS

(75) Inventors: Brent R. Constantz, Menlo Park, CA (US); Peter K. Johansson, Campbell, CA (US)

(73) Assignee: Cordis Corporation, Fremont, CA (US)

( * ) Notice: Subject to any disclaimer, the term of this patent is extended or adjusted under 35 U.S.C. 154(b) by 1876 days.

(21) Appl. No.: 11/295,677

(22) Filed: Dec. 5, 2005

(65) Prior Publication Data

US 2006/0178622 A1   Aug. 10, 2006

Related U.S. Application Data

(63) Continuation of application No. 10/284,044, filed on Oct. 29, 2002, now abandoned.

(51) Int. Cl.
*A61M 25/10* (2013.01)

(52) U.S. Cl.
CPC ........... *A61M 25/10* (2013.01); *A61M 25/1011* (2013.01); *A61M 2025/1013* (2013.01); *A61M 2025/1015* (2013.01); *A61M 2025/1052* (2013.01)
USPC ............... 604/101.05; 604/101.01; 604/96.01

(58) Field of Classification Search
CPC ............ A61M 25/10; A61M 25/1011; A61M 2025/1013; A61M 2025/1015; A61M 2025/1052; A61M 2025/1045
USPC ........ 604/96.01, 509, 101.01–101.04, 101.05
See application file for complete search history.

(56) References Cited

U.S. PATENT DOCUMENTS

| 4,808,153 A | 2/1989 | Parisi |
| 5,432,663 A | 7/1995 | Ichihara |
| 5,484,412 A * | 1/1996 | Pierpont .................. 604/101.03 |

(Continued)

FOREIGN PATENT DOCUMENTS

| WO | WO 00/03651 | | 1/2000 | |
| WO | WO 01/13985 | | 3/2001 | |
| WO | WO 01/15767 | * | 3/2001 | ............ A61M 31/00 |
| WO | WO 01/39783 | | 6/2001 | |

OTHER PUBLICATIONS

International Search Report for related Application No. PCT/US03/34480 dated Jun. 22, 2009.

*Primary Examiner* — Laura Bouchelle (57) ABSTRACT

Devices and methods for their use in increasing the aortic valve flow of a stenotic aortic valve are provided. The subject devices include an aortic valve isolation element and an aortic valve flushing element. The aortic valve isolation element is made up of a ventricular side aortic valve occlusion element, coronary ostia occlusion elements and an ascending aorta occlusion element. The aortic valve flushing element is made up of a dissolution fluid introducing element and a fluid removal element. In practicing the subject methods, a stenotic aortic valve is first isolated. Next, the isolated valve is flushed with a dissolution fluid, e.g., an acidic dissolution fluid, for a period of time sufficient for the aortic valve flow of the treated valve to be increased. In certain embodiments, the valve is also contacted with a dissolution fluid attenuating fluid, e.g., a buffer, during the flushing step in order to limit the contact of non-valve tissue with the dissolution fluid. Also provided are systems and kits that include the subject devices and can be employed in practicing the subject methods. The subject devices, methods, systems and kits find use in treating conditions associated with the presence of stenotic aortic valves.

1 Claim, 3 Drawing Sheets

(56) References Cited

U.S. PATENT DOCUMENTS

| | | | |
|---|---|---|---|
| 5,695,457 A * | 12/1997 | St. Goar et al. | 604/4.01 |
| 5,833,650 A | 11/1998 | Imran | |
| 6,117,105 A * | 9/2000 | Bresnaham et al. | 604/96.01 |
| 6,190,357 B1 | 2/2001 | Ferrari et al. | |
| 6,527,979 B2 | 3/2003 | Constantz et al. | |
| 6,533,767 B2 | 3/2003 | Johansson et al. | |
| 6,569,148 B2 * | 5/2003 | Bagaoisan et al. | 604/509 |
| 2004/0082910 A1 | 4/2004 | Constantz et al. | |

* cited by examiner

DEVICES AND METHODS FOR TREATING AORTIC VALVE STENOSIS

CROSS REFERENCE TO RELATED APPLICATIONS

This application is a continuation of and claims priority to U.S. patent application Ser. No. 10/284,044 filed Oct. 29, 2002, now abandoned. The complete disclosure of the aforementioned related U.S. patent application is hereby incorporated herein by reference for all purposes.

INTRODUCTION

1. Field of the Invention

The field of this invention is cardiology.

2. Background of the Invention

Aortic valve stenosis refers to a disease condition characterized by a narrowing of the aortic valve. While aortic valve stenosis can results from the presence of a bicuspid valve or rheumatic fever, wear and tear of the aortic valve in the elderly is the most common cause of this condition. This latter condition is known as "senile calcific aortic stenosis." With aging, protein collagen of the valve leaflets is destroyed, and calcium is deposited on the leaflets. Once valve leaflet mobility is reduced by calcification, turbulence across the valve increases, causing scarring, thickening, and stenosis of the valve.

Symptoms and heart problems in aortic stenosis are related to the degree of narrowing of the aortic valve area. Patients with mild aortic valve narrowing may experience no symptoms. When the narrowing becomes significant (usually greater that 50% reduction in valve area), the pressure in the left ventricle increases and a pressure difference can be measured between the left ventricle and the aorta. To compensate for the increasing resistance at the aortic valve, the muscles of the left ventricle thicken to maintain pump function and cardiac output. This muscle thickening causes a stiffer heart muscle which requires higher pressures in the left atrium and the blood vessels of the lungs to fill the left ventricle. Even though these patients may be able to maintain adequate and normal cardiac output at rest, the ability of the heart to increase output with exercise is limited by these high pressures. As the disease progresses, the increasing pressure eventually causes the left ventricle to dilate, leading to a decrease in cardiac output and heart failure. Without treatment, the average life expectancy after the onset of heart failure due to aortic stenosis is between 18 to 24 months.

When symptoms of chest pain, syncope, or shortness of breath appear, the prognosis for patients with aortic stenosis without valve replacement surgery is poor. Medical therapy, such as the use of diuretics to reduce high lung pressures and remove lung fluid, can provide only temporary relief of symptoms. Patients with symptoms usually undergo cardiac catheterization. If severe aortic stenosis is confirmed, aortic valve replacement is usually recommended. The overall mortality risk for aortic valve replacement surgery is about 5%.

While effective, aortic valve replacement is not without disadvantages, where such disadvantages include the requirement of chronic anticoagulation therapy, risk of failure and requirement for replacement, and the like.

As such, there is a continued interest in the development of new protocols for treating aortic valve stenosis.

Relevant Literature

See e.g., WO 01/15767; WO 01/13985; WO 00/03651; and WO 01/39783.

SUMMARY OF THE INVENTION

Devices and methods for their use in increasing the aortic valve flow of a stenotic aortic valve are provided. The subject devices include an aortic valve isolation element and an aortic valve flushing element. The aortic valve isolation element is made up of a ventricular side aortic valve occlusion element, coronary ostia occlusion elements and an ascending aorta occlusion element. The aortic valve flushing element is made up of a dissolution fluid introducing element and a fluid removal element. In practicing the subject methods, a stenotic aortic valve is first isolated. Next, the isolated valve is flushed with a dissolution fluid, e.g., an acidic dissolution fluid, for a period of time sufficient for the aortic valve flow of the treated valve to be increased. In certain embodiments, the valve is also contacted with a dissolution fluid attenuating fluid, e.g., a buffer, during the flushing step in order to limit the contact of non-valve tissue with the dissolution fluid. Also provided are systems and kits that include the subject devices and can be employed in practicing the subject methods. The subject devices, methods, systems and kits find use in treating conditions associated with the presence of stenotic aortic valves.

DETAILED DESCRIPTION OF THE INVENTION

Devices and methods for their use in increasing the aortic valve flow of a stenotic aortic valve are provided. The subject devices include an aortic valve isolation element and an aortic valve flushing element. The aortic valve isolation element is made up of a ventricular side aortic valve occlusion element, coronary ostia occlusion elements and an ascending aorta occlusion element. The aortic valve flushing element is made up of a dissolution fluid introducing element and a fluid removal element. In practicing the subject methods, a stenotic aortic valve is first isolated. Next, the isolated valve is flushed with a dissolution fluid, e.g., an acidic dissolution fluid, for a period of time sufficient for the aortic valve flow of the treated valve to be increased. In certain embodiments, the valve is also contacted with a dissolution fluid attenuating fluid, e.g., a buffer, during the flushing step in order to limit the contact of non-valve tissue with the dissolution fluid. Also provided are systems and kits that include the subject devices and can be employed in practicing the subject methods. The subject devices, methods, systems and kits find use in treating conditions associated with the presence of stenotic aortic valves.

Before the present invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Conversely, it is contemplated that the claims may be so-drafted to exclude any optional element. This statement is intended to serve as antecedent basis for use of such exclusive terminology as "solely," "only" and the like in connection with the recitation of claim elements or by use of a "negative" limitation The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides devices and methods for increasing the aortic valve flow of a stenotic aortic valve, as well as systems and kits for use in practicing the subject methods. In further describing the invention, the subject devices are described first in greater detail, followed by a review of the subject methods, systems and kits.

Devices

The subject invention provides devices that are capable of locally flushing an aortic valve in situ with a dissolution fluid. As such, the subject devices are capable of locally flushing an aortic valve when present in a heart, where the heart is generally present in a subject or patient (host). By "locally flushing" is meant that the aortic valve and, at most, the immediately adjacent tissue structures are flushed with the fluid, but not the remainder of the heart or host in which the subject aortic valve is present. As such, the subject devices do not systemically administer the dissolution fluid, such that it contacts the vasculature of the heart/host beyond the aortic valve.

The subject devices are also characterized in that they are dimensioned to be introduced into the aortic arch through a transverse aortotomy positioned upstream of the brachiocephalic trunk and downstream of the coronary ostia. As such, the size of the devices in many embodiments may not be sufficiently small for introduction into the vascular from a remote location, e.g., femoral approach, but is just small enough for insertion to an aortotomy as described above. Generally, the devices are dimensioned to be capable of insertion through an aortotomy that ranges in length from about 1 cm to 3 cm.

As summarized above, the subject devices include an aortic valve isolation element or system and a valve flushing element. Each of these elements is now described separately in greater detail.

Valve Isolation Element

The valve isolation element of the subject devices is made up of three different sub-elements that work in concert to isolate the target aortic valve to be treated from the remainder of the heart/vasculature of the host. By "isolate" is meant that the fluid flow between the target aortic valve and the remainder of the vascular system is substantially, if not completely, inhibited. As such, the valve isolation system effectively partitions the target aortic valve from the remainder of the vasculature. The three different sub-elements that make up the valve isolation element are: (1) a ventricular side valve occlusion element; (2) coronary ostia occlusion elements; and (3) an ascending aorta occlusion element. Each of these elements is now described in greater detail separately.

Ventricular Side Valve Occlusion Element

The ventricular side valve occlusion element serves to occlude blood flow through the aortic valve by blocking or occluding the upstream side of the valve, i.e., the ventricular side of the valve. This occlusion element may be any convenient type of occlusion element that can effectively occlude or block the ventricular site of the aortic valve. By effectively occlude or block is meant that fluid, e.g. blood, flow past the occlusion element upon activation is reduced by at least 95%, usually by at least 97% and more usually by at least 99%, where in preferred embodiments, fluid flow is reduced by 100% such that the fluid flow from the ventricle into the isolated valve site is substantially, if not completely, inhibited. Representative occlusion elements include inflatable balloons, expandable membranes, etc. In many embodiments, the occlusion element is an expandable or inflatable balloon. In these embodiments where the occlusion element is a balloon, the balloon is generally an expandable balloon that is capable of going from a first, compressed state to a second, expanded state, e.g., by introduction of a fluid or gas into the interior of the balloon, e.g., via an inflation lumen in fluid communication with the interior of the balloon. While the inflatable balloon may be one that is designed to be inflated with a gas or liquid, of particular interest in many embodiments are those that are configured to be inflated with a liquid, e.g. a pH elevating solution as described in greater detail infra. Balloons suitable for use in vascular devices, e.g., catheter devices, cannula devices, etc., are well known to those of skill in the art and may be readily adapted for use in devices of the present invention.

Coronary Ostia Occlusion Means

The next component of the isolation system is the coronary ostia occlusion element. This element blocks or occludes the coronary ostia at their opening into the aortic sinuses. More specifically, this occlusion element substantially, if not completely, blocks the flow of fluid from the aortic sinuses into the right and left coronary arteries by occluding the openings of these arteries. This occlusion element may be any convenient occlusion element, where representative occlusion elements of interest include, but are not limited to: balloons, non-porous membranes, elements for delivering degradable blocking compositions, e.g., biodegradable polymeric compositions, etc. In many embodiments, the coronary ostia occlusion element is made of two deployable balloons that are dimensioned for insertion into the entrance of the left and right coronary arteries and deployment upon insertion in a manner that substantially, if not completely, blocks fluid flow into the left and right coronary arteries.

Ascending Aorta Occlusion Element

The final sub-element of the isolation element is the ascending aorta occlusion element. This element serves to occlude fluid flow from the isolated valve into the ascending aorta downstream of its deployment. As such, the ascending aorta occlusion element is one that substantially, if not completely, impedes fluid flow past its site of deployment downstream into the aorta. Therefore, the occlusion means must be dimensioned upon deployment to substantially, if not completely, occlude the ascending aorta. This occlusion element is typically deployed at a location upstream of the brachiocephalic trunk, typically at least about 2 cm, usually at least about 20 mm upstream of the brachiocephalic trunk. Representative occlusion elements of interest include, but are not limited to: balloons, deployable non-porous membranes, etc.

Additional, Optional Features of the Valve Isolation Element

In addition to the above features, the valve isolation system may further include one or more of the following optional features. One optional feature of interest in certain embodiments is the provision of an element that provides for blood flow through the region of isolation. For example, the isolation element may further include a fluid passageway that conveys blood from the left ventricle through the isolated area to a position downstream of the ascending aorta occlusion element. Representative elements for accomplishing blood flow through the isolated region include, but are not limited to: tubes, and the like.

Valve Flushing Element

Also present in the subject devices is an aortic valve flushing element for flushing an isolated aortic valve with at least a dissolution fluid. By "flushing" is meant that fresh dissolution solution is contacted with the target valve surface one or more times, including continuously, during the treatment period, as described in further detail below, where in many preferred embodiments of the subject methods, the surface of the target valve surface, typically the aortic side of the aortic valve, is continuously contacted or flushed with the dissolution fluid. In other words, the acidic dissolution fluid is introduced in a manner such that a continuous flow of the dissolution fluid across the surface of the valve is achieved.

In flushing the isolated target valve, it is preferred that the pressure in the local environment which includes the isolated target valve (i.e. the area bounded by the ventricular side aortic valve occlusion means, the vessel walls of the aortic sinuses and that part of the aortic arch upstream from the ascending aorta occlusion means and the ascending aorta occlusion means) remains substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, the device includes a flushing element that dynamically contacts the target valve with dissolution fluid and simultaneously removes fluid from the local environment of the isolated valve, such that the overall volume of fluid in the local environment remains substantially constant, where any difference in volume at any two given times during the treatment period does not exceed about 50%, and usually does not exceed about 10%.

To provide for the above function, the flushing element of the subject devices typically includes a fluid introduction element and a fluid removal (i.e., aspiration) element, which elements are capable of introducing fluid into and removing fluid from the isolated local environment of the target aortic valve such that the aortic valve, or at least the aortic side thereof, is flushed with the introduced fluid. The fluid introduction and removal elements may take a variety of different configurations, so long as they serve their intended purpose of introducing fluid into and removing fluid from the isolated local environment of the target aortic valve. Representative configurations include, but are not limited to: two separate tubes or analogous fluid conveyance structures, where the tubes may or may not be concentric; two separate lumens of a single tube, e.g., a tube having a dividing partition running the length of the tube to define two separate fluid conveyance lumens; etc. As the fluid introduction and removal elements introduce and remove fluid from the local environment, they have distal openings that are positioned on the device upstream from the ascending aorta occlusion element. Depending on the particular configuration of the device, the distal openings of the fluid introduction and removal elements may or may not be positioned at the same location relative to the target valve.

The fluid introduction element is further characterized by having a proximal end that is either directly, or through a linking fluid conveyance structure, attached to a source of a dissolution fluid, e.g., a reservoir having a volume of dissolution fluid present therein, such that the interior of the fluid introduction means is in fluid communication with a volume of dissolution fluid. The proximal end of the fluid introduction element typically includes a valve or other flow control means for controlling the amount of the fluid that enters the lumen of the fluid introduction element from the reservoir of dissolution fluid.

The fluid removal or aspiration element is further characterized in that the fluid removal element is attached at its distal end, either directly or through a fluid conveyance linking element, e.g., tube, to a reservoir for waste fluid. In addition, a negative pressure element that provides for suction of fluid from the isolated local environment at the distal end of the fluid removal element into the fluid removal element is also present, where representative negative pressure elements include pumps, vacuums, etc.

In addition to the above fluid introduction and removal elements, in many embodiments the subject devices include a second fluid introduction element for introducing a second fluid into the isolated local environment of the target valve, where the second fluid delivery element is often an element for delivering a dissolution fluid attenuating fluid, as described in greater detail below. When present, the second fluid delivery element may be positioned or configured relative to the above described first fluid delivery and removal elements in a number of different ways. For example, the second fluid delivery element may be a separate tube or analogous structure, where the tube may or may not be present in one or more of the first fluid delivery element or aspiration element, or vice versa, e.g., the different elements may be concentric with each other. Alternatively, the second fluid delivery element may be a lumen present in a multi-lumen structure, where other lumens may be the aspiration and/or first fluid delivery elements.

The second fluid introduction element is further characterized by having a proximal end that is attached, either directly or through a linking fluid conveyance structure, to a source of a second fluid, e.g., a reservoir having a volume of dissolution fluid attenuating fluid present therein, such that the interior of the second fluid introduction means is in fluid communication with a volume of dissolution fluid attenuating fluid. The proximal end of the fluid introduction element typically includes a valve or other flow control element for controlling the amount of the fluid that enters the lumen of the second fluid introduction element from the reservoir of dissolution fluid attenuating fluid.

Additional General Features of the Device

The device may be a device in which all of the elements are statically positioned relative to each other such that no relative movement is possible between any two elements of the device, or two or more of the subject elements may be movable relative to each other in the device. For example, the fluid introduction element maybe slidably positioned inside of the fluid removal element; the ventricular side occlusion means may be adjustably movable relative to the remainder of the device to provide for an adjustable isolated local environment; etc.

The components of the subject devices, as described above, may be fabricated from any convenient material. The materials must be able to withstand contact with any fluids introduced or removed thereby and should be physiological compatible, at least for the period of time in which they are being used. Suitable materials include biocompatible polymers, e.g. polyimide, PBAX™, polyethylene, and the like. Any glues or fittings that are employed must also be able to meet the same criteria. Any convenient fabrication protocol may be employed, where numerous suitable protocols are known to those of skill in the art.

Representative Specific Embodiment

Figure 1:
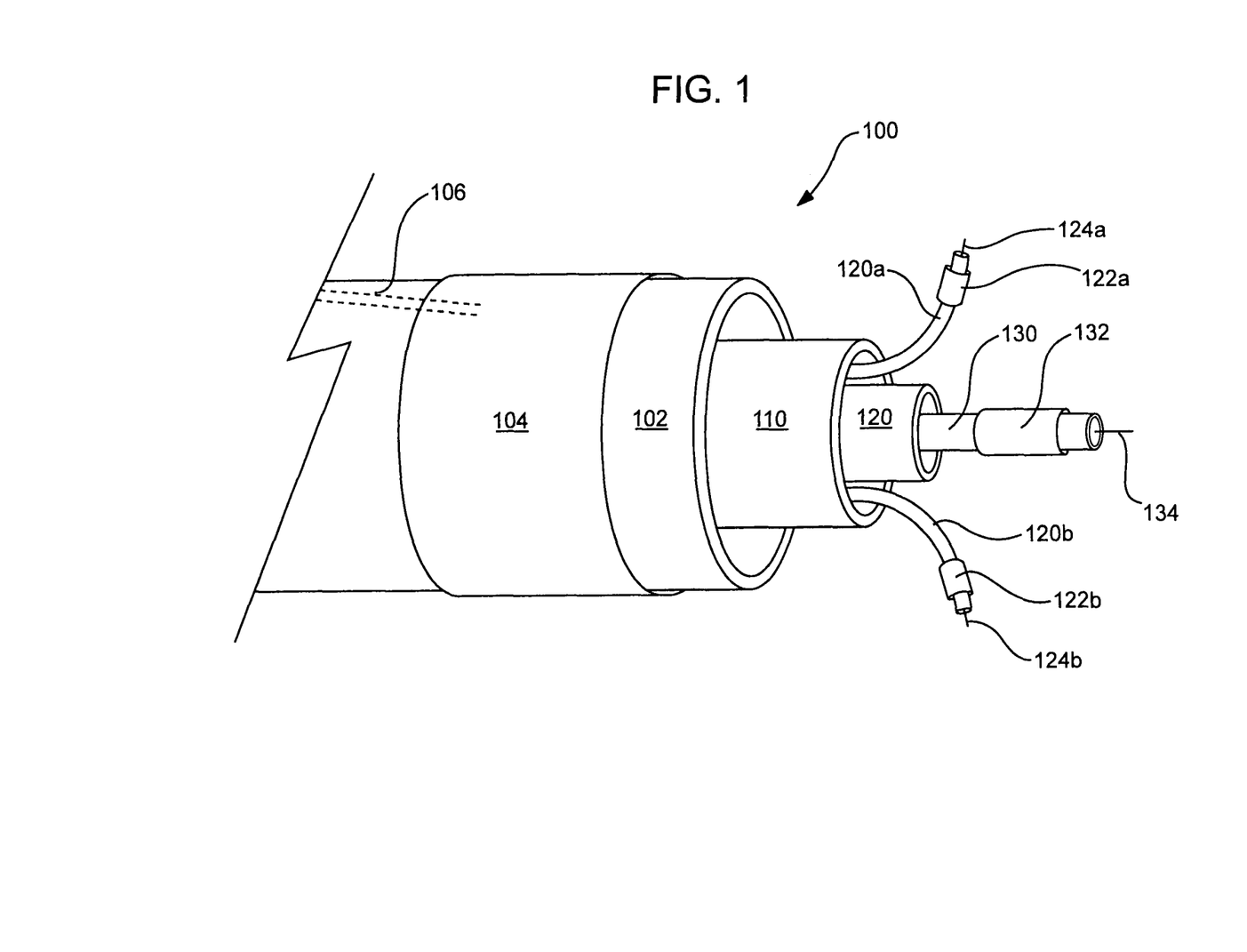
FIG. 1 provides an illustration of a device according to the subject invention.
Figure 2:
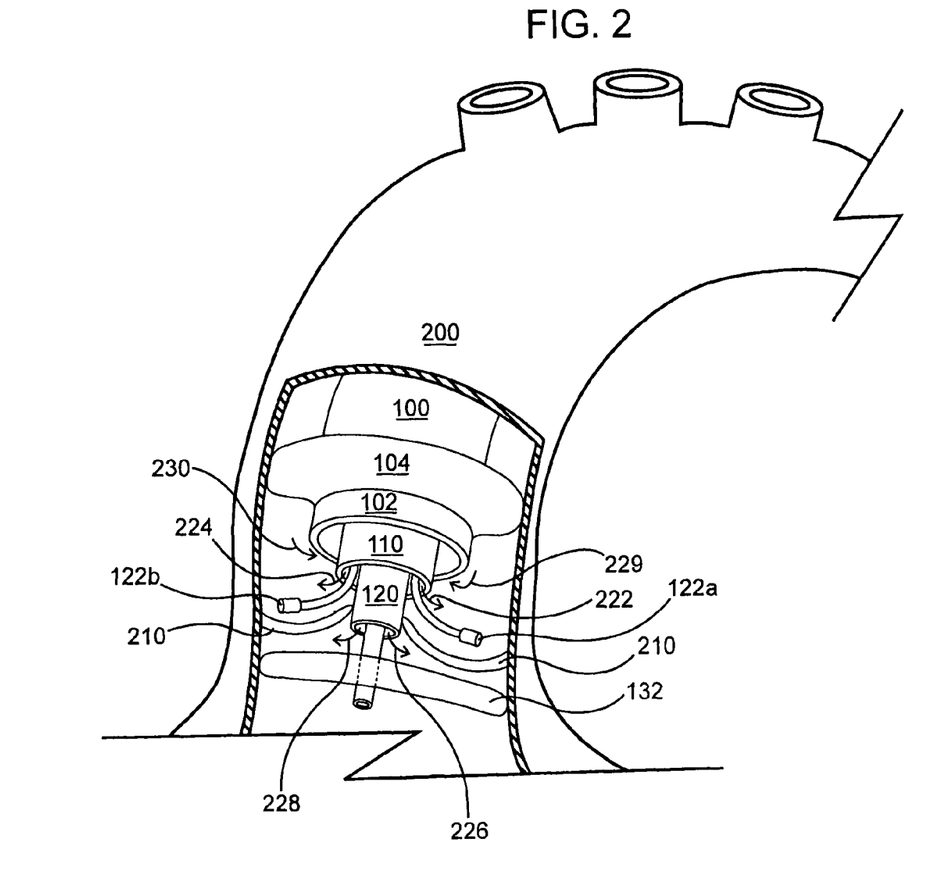
FIG. 2 provides an illustration of the device depicted in FIG. 1 in use.
Figure 3:
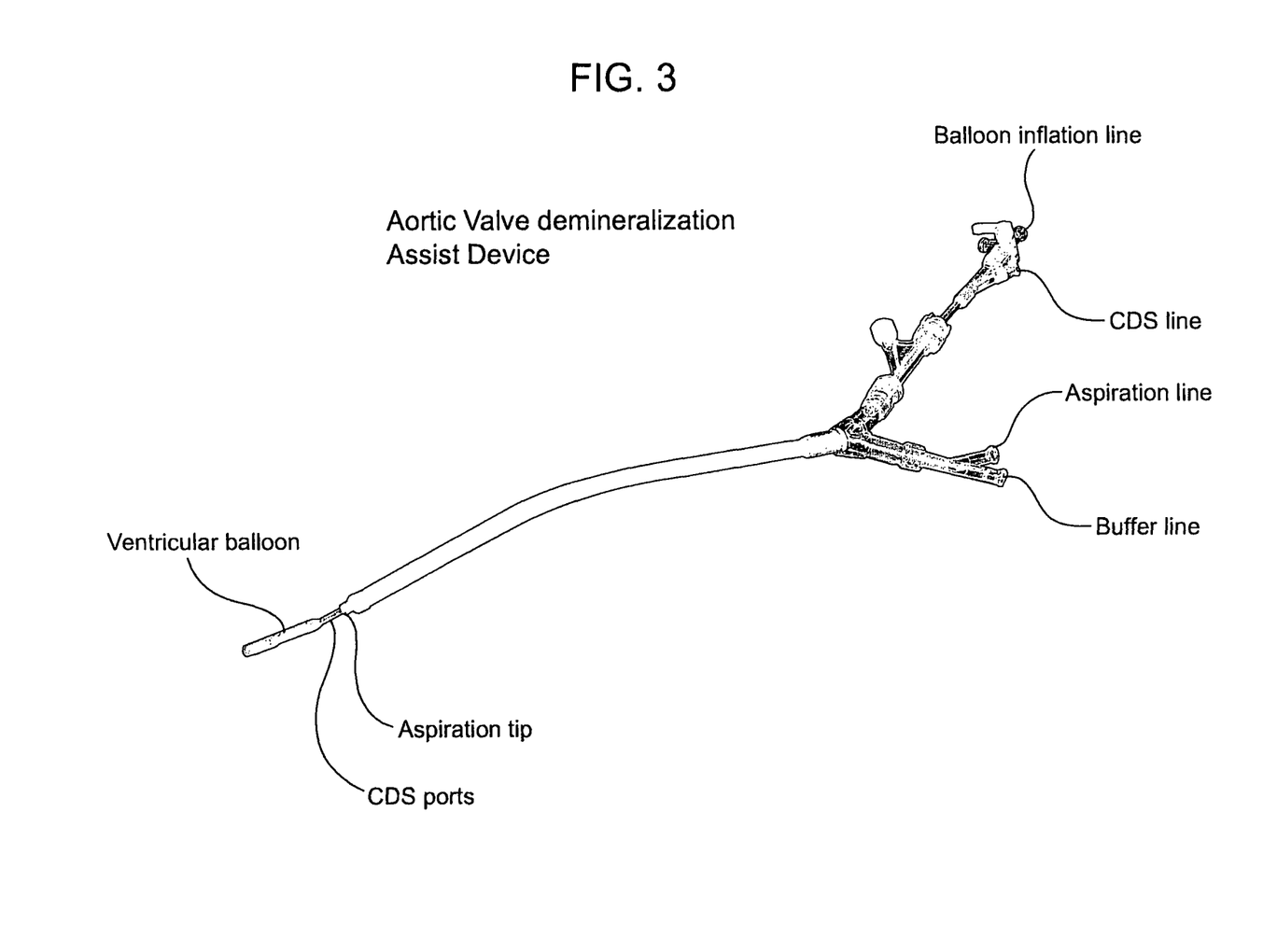
FIG. 3 provides a depiction of a prototype device according to the subject invention.

A representative embodiment of the subject devices is depicted in FIGS. 1 and 2. FIG. 1 provides a view of a device according to the subject invention prior to deployment. Device 100 includes fluid removal or aspiration tube 102. Aspiration element or tube 102 has an outer diameter ranging from about 3 mm to about 14 mm, usually from about 5 mm to about 9 mm; and an inner diameter ranging from about 2.75 mm to about 13.5 mm, usually from about 4 mm to about 8 mm.

Positioned on the outer surface of aspiration element 100 is the ascending aorta occlusion balloon 104 which is inflated and deflated by means of inflation lumen 106. Concentrically and slidably positioned inside of aspiration element 102 is first fluid delivery element 110, which serves to introduce a dissolution fluid to the isolated aortic valve during use. The volume to which balloon element 104 should be expandable is sufficient to occlude the ascending aorta upon deployment, and typically ranges from about 10 mm to about 35 mm, usually from about 22 mm to 28 mm. In certain embodiments, it is desirable to limit the volume to which the balloon may be expanded so that tissue/vessel damage does not inadvertently occur upon deployment/use, where this volume limit generally does not exceed about 20 cc and usually does not exceed about 10 cc.

Concentrically and slidably positioned within aspiration element 102 is first fluid delivery element 110. The outer diameter of first fluid delivery element typically ranges from about 2.5 mm to about 12 mm, usually from about 3 mm to about 7 mm; while the inner diameter typically ranges from about 2 mm to about 11.5 mm, usually from about 2.5 mm to about 6.5 mm.

Slidably though not concentrically positioned within first fluid delivery element 110 are coronary ostia occlusion elements 120a and 120b. Each of these elements includes a balloon at their distal end, 122a and 122b, and a guidewire, 124a and 124b. In many embodiments, these occlusion elements can be retracted or extended from the lumen of the first fluid delivery element 110 in order to position the occlusion balloons at the entrances of the coronary ostia.

Concentrically and slidably positioned within first fluid delivery element 110 is second fluid delivery element 120. This fluid delivery element has an outer diameter ranging from about 1.75 mm to about 11 mm, usually from about 2 mm to about 6 mm; and an inner diameter ranging from about 1.5 mm to about 10.5 mm, usually from about 1.75 mm to about 5.75 mm.

Concentrically and slidably positioned within second fluid delivery element 120 is ventricular side aortic valve occlusion element 130, which includes balloon 132. The outer diameter of this element typically ranges from about 1.25 to about 11 mm, usually from about 1.5 mm to about 6.5 mm. The volume to which balloon element 132 should be expandable is sufficient to occlude the ventricular side of the aortic valve from the remainder of the left ventricle upon deployment, and typically ranges from about 20 mm to about 40 mm, usually from about 25 mm to 30 mm. Guidewire 134 is also shown.

Methods

The above-described devices find use in methods of flushing an aortic valve with at least one fluid composition. In the broadest sense, the subject catheter systems may be employed to introduce any active agent in a fluid delivery vehicle to an aortic valve by flushing the aortic valve with such a fluid composition. The subject systems achieve local delivery of active agents in fluid delivery vehicles by irrigating or flushing an isolated aortic valve with the fluid agent composition.

Of particular interest are methods of using the subject devices to flush an isolated aortic valve, particularly a stenotic aortic valve, with a dissolution fluid, where the dissolution fluid may be an organic matter dissolution fluid or an inorganic matter dissolution fluid, or a fluid that is capable of both inorganic matter and organic matter dissolution. Representative dissolution fluids are described in copending U.S. patent application Ser. No. 09/774,469; the disclosure of which is herein incorporated by reference.

In many embodiments, the dissolution fluid employed in the subject methods is an inorganic matter dissolution solution. In many of these embodiments, the inorganic matter dissolution fluid is an acidic dissolution fluid. A variety of different types of acidic dissolution solutions may be employed in the subject methods. The acidic treatment solutions that find use in the subject methods generally have a pH of less than about 6.5, where the pH is usually less than about 4.0 and more usually less than about 3.0.In many preferred embodiments, the pH ranges from 0 to 2, and usually 0 to 1.The acidic treatment solution can include a number of different types of acids, where the acids may or may not include a hydrocarbon moiety, i.e., a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osomolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

In certain embodiments of the subject methods, e.g., those embodiments in which a device having two fluid delivery elements, in addition to the dissolution solution, the target aortic valve is also contacted with a dissolution solution attenuating fluid. The nature of the dissolution solution attenuating fluid necessarily depends on the nature of the dissolution fluid, where representative pairs of fluids and their attenuating counterparts are described in U.S. patent application Ser. No. 09/774,469, the disclosure of which is herein incorporated by reference.

Where the dissolution fluid is an acidic dissolution fluid, attenuating fluids of particular interest are pH elevating fluids. By pH elevating solution is meant any solution that, upon combination with the acidic dissolution solution, produces a solution with an elevated pH with respect to the acidic dissolution solution. In principle, any fluid that, upon combination of with the acid dissolution fluid produces a solution having a pH higher than that of the acidic dissolution fluid, may be employed, so long as the fluid is biocompatible, at least for the period of time that it is present in the target vascular site. The pH elevating solution should have a pH of at least about 4, usually at least about 6 and more usually at least about 8. As such, pH elevating fluids of interest include water, physiological acceptable buffer solutions, etc., where in many embodiments, the pH elevating solution is a buffer solution. Representative buffer solutions of interest include: phosphate buffered saline, sodium bicarbonate and the like.

In practicing the subject methods, the first step is to prepare the host or patient for the procedure. In many embodiments, the host is prepared by placing the host on cardio pulmonary bypass followed by arrest of the heart, e.g., via introduction of a cardoplegia solution to the heart. These procedures are well known to those of skill in the art in the field of cardiology, particular coronary artery bypass graft (CABG) surgery. See e.g., U.S. Pat. No. 6,190,357; the disclosure of which is herein incorporated by reference.

Following preparation of the host/patient/subject, the device is placed in position such that, upon deployment, the target aortic valve can be isolated from the remainder of the vasculature with the device. In this step, access is first provided to the ascending aorta so that the requisite aortotomy used to introduce the distal end of the device into the aortic root can be cut. Access can be provided using any convenient protocol, including via open chest, an opening produced through the appropriate ribs, etc. Once access is provided, the aortotomy is produced. The aortotomy is produced in the wall of the ascending aorta a point upstream from the brachiocephalic trunk. The length of cut made in the aortic wall may vary depending on the dimensions of the device being employed, but typically ranges in many embodiments from about 5 mm to about 15 mm, usually from about 7 mm to about 12 mm and more usually from about 8 mm to about 10 mm.

Following production of the aortotomy, the device is inserted through the opening into the lumen of the aortic root/ascending aorta. The inserted device is advanced in a retrograde fashion such the distal end of the device extends through the aortic valve into the left ventricle. Following proper positioning of the distal end of the device into the left ventricle, the isolation elements of the device are then deployed in a manner sufficient to substantially, if not completely, isolate the to be treated aortic valve from the remainder of the vasculature of the host. The particular manner of deployment necessarily depends on the nature of the isolation system of the device. For example, where the isolation elements that make up the isolation system of the device are inflatable balloons, the isolation step includes a step of inflating the various balloons. The balloons may be inflated simultaneously or sequentially, as may be desired or indicated depending on the particular procedure being performed. For example, the ventricular side aortic valve occlusion balloon may be inflated first, followed by inflation of the ascending aorta occlusion balloon and the coronary ostia occlusion balloons.

The above protocol results in an isolated target aortic valve. FIG. 2 provides an illustration of an isolated target aortic valve produced by deployment of a device in accordance with the subject invention. As seen in FIG. 2, cutaway view of the ascending aorta/aortic root 200 shows device 100 positioned therein, where the device has been inserted via an aortotomy (not shown). Ventricular side occlusion element 132 is inflated on the ventricular side of aortic valve 210. Ascending aorta occlusion balloon is also inflated so as to prevent fluid flow beyond the balloon into the remainder of the aorta. Finally, ostia occlusion balloons 122a and 122b are inflated and positioned over the coronary ostia so as to preclude fluid flow into the coronary ostia. As such, the aortic valve is isolated from the remainder of the vasculature of the patient.

Following isolation of the aortic valve, the isolated aortic valve is then flushed with at least the dissolution fluid, e.g., an acidic dissolution fluid, and in many embodiments is simultaneously flushed with the dissolution fluid and a dissolution fluid attenuating fluid. As the isolated valve is flushed with the dissolution fluid, it is dynamically contacted with the dissolution fluid. By "dynamically contact" is meant that the fresh dissolution solution is contacted with the surface of valve one or more times, including continuously, during the treatment period. In many preferred embodiments of the subject methods, the surface of the valve is continuously contacted or flushed with the acidic dissolution fluid. In other words, the acidic dissolution fluid is introduced in a manner such that a continuous flow of the acidic dissolution fluid across the surface of the valve is achieved. While both the ventricular and aortic surfaces of the valve may be contacted with the dissolution fluid, in many embodiments the aortic surface and commissurs are contacted with the dissolution fluid, with substantially less fluid contact of the ventricular surface of the valve, if any.

In flushing with the dissolution fluid, it is preferred that the pressure in the local environment which includes the aortic valve, i.e. the area bounded by the walls of the aortic root and the occlusion means of the isolation element, remains substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, where fluid is dynamically contacted with the surface of the aortic valve surface, fluid is also simultaneously removed from the local environment, such that the overall volume of fluid in the local environment remains substantially constant, where any difference in volume at any two given times during the treatment period does not exceed about 50%, and usually does not exceed about 10%. As such, the dissolution fluid is introduced into the local environment of the isolated valve in a manner such that the local environment remains substantially isovolumetric.

When flushing the aortic valve with the dissolution fluid, the dissolution fluid is introduced in a manner such that the flow rate of the dissolution solution through the local environment is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by "volume" is meant the local environment of the isolated aortic valve, as defined above. The total amount of dissolution fluid that is passed through the local environment during the treatment period typically ranges from about 100 to 1000 cc, usually from about 200 to 800 cc and more usually from about 400 to 500 cc. The solution is generally pressurized to achieve the desired flow rate, as described supra. As such, the pressure at the distal end of the dissolution fluid fluid delivery element through which the dissolution fluid is introduced into the local environment typically ranges from about 50 to 1200 psi, usually from about 100 to 600 psi and more usually from about 200 to 400 psi. It is important to note that the overall pressure in the local environment is maintained at substantially isometric or isobaric conditions. As such, the negative pressure at the entrance to the aspiration element or fluid removal means is of sufficient magnitude to provide for substantially isobaric conditions. Preferably, the overall pressure in the local environment is maintained at a value ranging from about 0.1 to 3 psi, usually from a bout 0.5 to 2.5 psi and more usually from about 1 to 2 psi.

In many embodiments, a feature of the subject methods is that the isolated local environment is flushed with a dissolution fluid attenuating fluid, e.g., a pH elevating solution, concomitantly or simultaneously with the acidic dissolution fluid in a manner sufficient such that only the aortic surface of the artic valve, and not the remainder of the tissue present in the isolated local environment, is contacted with a low pH solution. As such, the remainder of the isolated local environment or vascular site is contacted with a fluid that has a pH well above that of the acidic dissolution fluid, where the lowest pH to which the remainder of the target vascular site is subjected is not less than 4, preferably not less than 5 and more preferably not less than 6.In other words, only the aortic surface of the target valve is contacted with the low pH acid dissolution fluid while the remainder of the target vascular site, e.g., the ventricular side, the coronary ostia, the intimal surface of the aortic sinuses, etc., is contacted with a solution the pH of which is not less than 4, preferably not less than 5 and more preferable not less than 6.

FIG. 2 provides an illustration of an isolated aortic valve being flushed with an acidic dissolution fluid and a buffer simultaneously. In FIG. 2, arrows 222 and 224 show acidic dissolution fluid leaving the distal opening of the dissolution fluid delivery tube 110. As can be seen, dissolution fluid leaves the distal end opening of tube 110 and contacts the aortic side of isolated valve 210. In addition, second fluid delivery element delivers buffer solution indicated by arrows 226 and 228 to the ventricular side of the isolated aortic valve 210. Fluid is also removed from the isolated local environment as indicated by arrows 229 and 230 into the distal end of aspiration element 102.

The isolated aortic valve is flushed with at least the dissolution fluid, and in many embodiments the dissolution fluid attenuating fluid, for a period of time sufficient to achieve the desired result. The desired result necessarily depends on the application being performed, where representative desired results are described below in the section entitled "Utility." While the period of time that the valve is flushed may vary, the period of time typically ranges from about 15 minutes to about 2 hours, usually from about 20 minutes to about 30 minutes and more usually from about 25 minutes to about 30 minutes.

Following flushing for the desired period of time, the device is then removed from the patient. The device may be removed using any convenient protocol. In one representative protocol, the occlusion balloons are deflated and then the device is removed from the ascending aorta through the aortotomy. The patient may then be removed from heart/lung bypass and the heart may be started using conventional procedures, followed by surgical closing and post-operative care standard to those of skill in the art.

Optional Method Steps

In a number of embodiments of the subject methods, the above described methods may be modified to include a number of additional method steps. Additional method steps that may be present in the overall process include: rendering the local environment of the isolated aortic valve bloodless, washing or rinsing the isolated local environment of the aortic valve, applying external energy to the aortic valve during treatment; imaging the isolated vascular site; and the like.

Rendering the Local Environment Bloodless

In many preferred embodiments, as described above, the local environment of the aortic valve is rendered substantially bloodless prior to introduction of the acidic dissolution fluid.

In these embodiments, the isolation system is deployed to physically isolate the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g. Ringer's, phosphate buffered saline, or other physiologically acceptable solutions. The washing solution may include an anti-clotting factor in many embodiments, where anticlotting factors of interest include heparin and the like. The washing solution can also contain chelating agents.

Application of External Energy

In certain embodiments, external energy is applied to the target aortic valve to promote mechanical break-up of the calcified deposits into particles or debris that can be easily removed from the vascular site. Any means of applying external energy to the aortic valve may be employed. As such, jets or other such means the device which are capable of providing varying external forces to the target deposits cause the target deposit to break up or disrupt may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the target occlusion. There are several devices for the application of ultrasound to cardiovascular tissue known to those of skill in the art. See e.g. U.S. Pat. Nos. 4,808,153 and 5,432,663, the disclosures of which are herein incorporated by reference.

Another means that may be employed to apply external energy to the lesion during the dissolution process is to use a mechanical means of applying external energy. Mechanical means of interest include moving structures, e.g. rotating wires, guidewires, which physically contact the target occlusion and thereby apply physical external energy to the target lesion.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the vascular site before, during or after contact with the dissolution fluid.

In many embodiments, an imaging agent is employed, where the imaging agent may or may not be present in the acidic dissolution solution. Imaging agents of particular interest include: non-ionic imaging agents, e.g. CONRAY™, OXILAN™, and the like.

Utility

The above described methods and devices find use in any application in which it is desired to contact an isolated aortic valve with a fluid, e.g., a fluid composition of a therapeutic agent. The subject devices and methods are particularly suited for use in the treatment of aortic stenosis. The term "aortic stenosis" is used broadly to refer to any condition that is characterized by disease and narrowing of the valve such that fluid flow through the valve is impeded. In many instances, the target aortic stenosis condition of the subject methods is characterized by having calcification present on the valve leaflets that reduces or impedes mobility of the leaflets. Of particular interest is the treatment of aortic stenosis characterized by calcified deposits on the leaflet surface in which the calcification results in a aortic valve flow (as measured by the cardiac catheterization technique known in the art as the gold standard for evaluating aortic stenosis) that is less then 3.0, often less than about 2.5 and more often less than about 2.0, where in many embodiments the aortic valve flow may be less than 1.0.

Treatment of aortic stenosis according to the subject invention results in at least a reduction in the amount of calcium phosphate mineral present on a stenotic valve surface, i.e., the aortic side leaflet surface. The amount of reduction that is achieve with the subject invention is typically at least about 10%, usually at least about 20% and more usually at least about 30% by weight.

In many embodiments, treatment according to the subject methods results in an increase in aortic valve flow, as determined using the cardiac catheterization protocol described above. The amount of increase that is achieve is generally at least about 0.5 units, usually at least about 1.0 unit. In many embodiments, the aortic valve flow is improved to a value that is at least about 1, preferably at least about 1.5 and more preferably at least about 2.0, where one may achieve even higher values, including the normal 3.0, in certain embodiments.

Treatment also typically results in amelioration of one or more symptoms associated with, e.g., caused by, aortic stenosis, including but not limited to: chest pain, fainting, shortness of breath, delayed upstroke and lower intensity of the carotid pulse, heart murmur, abnormal EKG patterns, etc.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Systems

Also provided by the subject invention are systems for practicing the subject methods, i.e. for flushing an aortic valve with a fluid, e.g., to treat an aortic valve stenosis as described above. The subject systems at least include the subject devices as described above, a fluid reservoir for storing acidic dissolution fluid, a fluid reservoir for storing a pH elevating fluid and a negative pressure means for providing aspiration or suction during use of the system. The systems may further include a number of optional components, e.g. guidewires, pumps for pressurizing the dissolution fluid, and the like. See e.g. U.S. patent application Ser. No. 09/384,860, the disclosure of which is herein incorporated by reference.

Kits

Also provided by the subject invention are kits for use in treating a patient suffering from aortic stenosis. The subject kits at least include a device as described above. The kits may further include one or more additional components and accessories for use with the subject devices, including tubing for connecting the various components with fluid reservoirs, syringes, pumping means, etc., connectors, one or more guidewires, dilators, vacuum regulators, etc.

In certain embodiments, the kits further include one or more solutions, or precursors thereof, where in such embodiments the kits at least include an acidic dissolution fluid, such as a hydrochloric acid solution, as described above, where the solution may be present in a container(s), e.g. a flexible bag, a rigid bottle, etc. For kits that are to be used in methodologies in which the fluid is flushed through the local environment of the lesion, the amount of dissolution fluid present in the kit ranges from about 0.5 to 500 liters, usually from about 0.5 to 200 liters and more usually from about 0.5 to 100 liters. In many embodiments, the amount of dissolution fluid in the kit ranges from 0.5 to 5 liters, usually from about 0.5 to 2.0 liters and more usually from about 0.5 to 1.5 liters. Alternatively, the kit may comprise precursors of the dissolution solution for use in preparing the solution at the time of use. For example, the precursors may be provided in dry form for mixing with a fluid, e.g. water, at the time of use. In addition to the dissolution fluid or precursors thereof, the kit may further comprise one or more additional fluids (or dry precursors thereof), such as a priming solution, a washing solution, contrast medium, and the like. In many embodiments, the kits further include at least a pH elevating solution, e.g. a buffer solution such as phosphate buffered saline.

Other elements that may be present in the subject kits include various components of the systems, including manifolds, balloon inflation means, e.g. syringes, pumping means, negative pressure means etc.

In addition to above mentioned components, the subject kits typically further include instructions for using the components of the kit to practice the subject methods with the subject devices. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion and results that improved methods of treating aortic stenosis are provided. The subject methods and devices provide for significant advantages in the treatment of this condition in that prosthetic elements need not be employed, as the subject's own aortic valve is maintained and restored to function. In addition, the subject methods may be less traumatic to the patent that convention valve replacement protocols. Additional advantages include a delay in the need for valve replacement. As such, the subject invention represents a significant contribution to the field.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for treating aortic valve stenosis utilizing a dissolution fluid, the device comprising:
    a fluid aspiration element having a substantially tubular shape;
    an ascending aortic occlusion element positioned around an outer surface of the fluid aspiration element and sized to occlude the ascending aorta;
    a first fluid delivery element having a substantially tubular configuration and arranged slidably and concentrically within the fluid aspiration element creating a first annular gap therebetween;
    a second fluid delivery element having a substantially tubular configuration and arranged slidably and concentrically within the first fluid delivery element creating a second annular gap therebetween;
    coronary ostia occlusion elements positioned in the second annular gap between the first and second fluid delivery elements, each element having a balloon dimensioned for insertion into the entrance of the left and right coronary arteries and a guidewire lumen;
    a ventricular side aortic valve occlusion element positioned slidably and concentrically within the second fluid delivery element, the ventricular side aortic valve occlusion element having a balloon dimensioned to occlude the ventricular side of the aortic valve and a guidewire lumen; and
    a guidewire disposed within the guidewire lumen of the ventricular side aortic valve occlusion element.

* * * * *